United States Patent [19]

Mück et al.

[11] Patent Number: 5,401,859
[45] Date of Patent: Mar. 28, 1995

[54] PROCESS FOR THE PREPARATION OF PURE TRIOXANE

[75] Inventors: Karl Mück, Wiesbaden; Helmut Schlaf, Kelkheim/Ts.; Siegbert Rittner, Mörfelden, all of Germany

[73] Assignee: Hoechst AG, Frankfurt, Germany

[21] Appl. No.: 72,761

[22] Filed: Jun. 7, 1993

[30] Foreign Application Priority Data

Jun. 6, 1992 [DE] Germany .................. 4218735.4

[51] Int. Cl.⁶ .......................................... C07D 323/06
[52] U.S. Cl. .................................................. 549/368
[58] Field of Search ...................................... 549/368

[56] References Cited

U.S. PATENT DOCUMENTS

| | | | |
|---|---|---|---|
| 3,281,336 | 10/1966 | Talbert | 549/368 |
| 3,519,650 | 7/1970 | Fleck et al. | 549/368 |
| 4,189,565 | 2/1980 | Sugio et al. | 549/368 |

FOREIGN PATENT DOCUMENTS 7033407  12/1964  Japan.

OTHER PUBLICATIONS

Morimoto, R., et al, Chem. Abs. 74:64634v (1971).
Winnacker–Kuchler, Chemische Technologie, 4th Ed., vol. 6, Carl Hanser Verlag, Munich, 1982, pp. 145–150.

Primary Examiner—C. Warren Ivy
Assistant Examiner—Raymond Covington
Attorney, Agent, or Firm—Connolly and Hutz

[57] ABSTRACT

In the process for the preparation of pure trioxane by continuous or semicontinuous crystallization processes, if alkaline organic compounds are added no flocks appear after more than 120 hours of operation. As a result, blockage of the crystallization unit is prevented and problem-free running is made possible.

13 Claims, No Drawings

PROCESS FOR THE PREPARATION OF PURE TRIOXANE

DESCRIPTION

Process for the preparation of pure trioxane

The invention relates to a process for the preparation of pure trioxane by a crystallization process, in which alkaline organic compounds are added.

According to the prior art, a multiplicity of steps are used in the preparation of trioxane. Thus, it is usually prepared by heating 30–70 % strength aqueous formaldehyde solutions in the presence of acidic catalysts, e.g. 2–25 % mineral acid (DE-B 1 543 390), or in the presence of acidic ion exchangers (DE-C 1 135 491) and then removed from the reaction mixture by distillation. This is carried out either in a column attached to the reactor (U.S. Pat. No. 2,304,080) or in a separate column (GB-B 1 012 372). The trioxane-rich distillate is extracted with methylene chloride, ethylene chloride, benzene or toluene (DE-B 1 668 867), and the extract is then neutralized and purified by distillation (DE-B 1 543 815).

The extraction mentioned is necessary in order to achieve the removal of the trioxane from the water, while said purification by distillation is necessary in order to remove by-products formed during trioxane synthesis, such as formaldehyde, methanol, formic acid, methyl formate, methylal, dioxymethylene dimethyl ether and others, and thus to obtain a polymerizable trioxane.

It is also known to achieve the removal of impurities in the trioxane by extractive distillation in the presence of water or ethylene glycol (U.S. Pat. No. 3,281,336).

To remove the impurities, it is also possible to crystallize liquid trioxane in an open system and to move air or an inert gas, possibly under elevated pressure, over it (DE-A 2 885 710). By passing over air, however, new impurities such as peroxide can be formed in the trioxane.

Additionally, mainly only the low-boiling impurities are removed by this procedure. High-boiling components, which can likewise interfere in the polymerization, still remain in the product in significant amounts. The high sublimation pressure of the trioxane also has a disadvantageous effect in the process described in that losses of material occur.

DE-A 3 508 668 describes the preparation of polymerizable trioxane in high purity by multi-step crystallization. It has now been observed that, with a trioxane content of above 95%, after many hours of operation or crystallization cycles formation of flocks can occur which is so severe that the entire crystallization unit becomes blocked.

The object was therefore to make available a process for the crystallization of trioxane which on the one hand produces polymerizable trioxane in high purity and on the other hand prevents formation of flocks.

The invention thus relates to a process for the preparation of highly pure trioxane by crystallization of a trioxane mixture, which comprises adding alkaline organic compounds to the trioxane mixture during the crystallization.

It is surprising that, in spite of addition of alkaline organic compounds, which in general inhibit the trioxane polymerization, the pure trioxane obtained is polymerizable and high molecular weight polymers can be prepared from this by cationic polymerization.

The crystallization of the trioxane can be carried out by various methods, which are known in the literature, and in various types of crystallizers. It is essential that the crystallization is accompanied by at least one process step corresponding to a washing or sweating operation, which removes the added components from the crystallizate simultaneously. Continuous, batchwise and semicontinuous crystallization processes are suitable for the process according to the invention. Continuous crystallization processes, as are described in EP-B 0 105 524, and semicontinuous crystallization processes, as are described in DE-A 3 508 668 and to which reference is hereby made, are particularly suitable. Depending on the degree of purity of the trioxane employed and possibly on the apparatus used, the crystallization can be carried out in one or more steps.

It is essential to add the alkaline organic component added to the process in the crystallization step or in the apparatus section in which the purity of the trioxane has reached a certain level. This is in general in the range from 95 to 99.9% by weight, preferably 98 to 99.9 and in particular 99.3 to 99.9% by weight.

Suitable alkaline organic components in the present process are amines. Tertiary amines having a distinctly higher boiling point compared to trioxane are preferred. Triethanolamine, tripropylamine, methyldiethanolamine and dimethylethanolamine and mixtures thereof, but in particular triethanolamine, may be especially mentioned here.

The amount of amine added is in general 500 to 5 ppm, relative to pure trioxane, and the concentration range from 100 to 5 ppm and in particular from 25 to 5 ppm is preferred.

The amines employed prevent formation of flocks during the crystallization process. They are removed again in the purification steps of the process (sweating, washing) to such an extent that they are analytically no longer detectable and the polymerizability of the pure trioxane is thus not impaired.

Examples

Examples 2 and 3 and the Comparison Example were carried out by the following process:

In a moisture-free tubular crystallizer inertized with nitrogen (Winnacker-Küchler, Chemische Technologie (Chemical Technology), 4th Ed., Volume 6 (1982) p. 148), whose jacket was attached to a thermostat having a temperature programmer, molten, 94% pure trioxane (additionally contains water, formaldehyde, methanol and the further afore-mentioned by-products) was initially introduced and purified by crystallization. To do this, the product was cooled to 50° C. in the course of 30 minutes and the liquid fraction was drained. The crystals remaining in the apparatus, which have a degree of purity of above 95%, were melted and subjected to a further similar crystallization process. In general, the 94% pure trioxane purified in this way in two steps has a degree of purity of above 99.9% and is thus suitable for a polymerization in the conventional sense.

1. (Comparison Example)

This procedure was operated continuously for 24 hours. After this time, polymer flocks appeared in the molten trioxane, which were very voluminous and blocked outlet valves and distributors of the crystallization apparatus. The total amount of flocks was around 1% b.w., based on trioxane.

2. Triethanolamine addition in the 2nd crystallization step (20 ppm, relative to trioxane)

If 20 ppm of triethanolamine, relative to trioxane, are added in the continuous procedure to the crystallization step at a trioxane content of above 95%, no flocks appear during an experimental period of 120 hours.

3. Triethanolamine addition in the 2nd crystallization step (100 ppm, relative to trioxane)

The amount of triethanolamine is increased compared to Example 2 to 100 ppm. Formation of flocks did not appear during the experimental period of 120 hours.

The highly pure trioxane obtained from Experiments 1 to 3 was optionally filtered from the flocks (Comparison Experiment 1) and in each case mixed with 3.4 % by weight of dioxolane. In a closed aluminum tube, the monomer mixtures were temperature-controlled at 80° C. in a liquid bath and $BF_3$ etherate, diluted in cyclohexane, was added to the three samples by means of an injection syringe. The monomer and the initiator were intimately mixed by shaking. In addition to the induction period up to the onset of polymerization, the yield of polymer and the melt index of the particular polymer were determined.

The results are compiled in the table.

Polymerization of trioxane in tubes (after purification by crystallization) at 80° C. in the presence of $BF_3$ etherate $\hat{=}$ 13 ppm of $BF_3$)

| Example | Amine addition during the crystallization | Induction period (sec) | Melt index MFI DIN 53735 | Yield % | Amine content ppm |
|---|---|---|---|---|---|
| 1. Comparison | — | 53 | 2.6 | 95 | — |
| 2. | +20 ppm | 52 | 2.8 | 94 | <5 |
| 3. | +100 ppm | 55 | 2.4 | 93 | <5 |

We claim:

1. A process for the preparation of a highly pure trioxane by crystallization of a trioxane mixture, which comprises adding an amine to a crystallization step or to a crystallization apparatus section in which in both the purity of the starting trioxane is at least 95% by weight, said crystallization is accompanied by at least one process step corresponding to a washing or sweating operation.

2. A process as claimed in claim 1, wherein the crystallization is effected in one or more steps.

3. The process as claimed in claim 1, wherein the amine employed is a tertiary amine having a distinctly higher boiling point compared to trioxane.

4. The process as claimed in claim 3, wherein said tertiary amine is triethanolamine, tripropylamine, methyldiethanolamine, or dimethylethanolamine or a mixture thereof.

5. The process as claimed in claim 3, wherein said tertiary amine comprises triethanolamine.

6. The process as claimed in claim 1, wherein the purity of the starting trioxane is 95 to 99.9% by weight.

7. The process as claimed in claim 6, wherein the purity of the starting trioxane is 99.3 to 99.9% by weight.

8. The process as claimed in claim 1, wherein the the amine content of the trioxane mixture during the crystallization is 5 to 500 ppm, relative to pure trioxane.

9. The process as claimed in claim 8, wherein the amine content is 5 to 25 ppm.

10. A process for the preparation >95 weight-% pure trioxane by multi-step crystallization of an impure trioxane containing up to about 5 weight-% impurities, comprising:

carrying out the multi-step crystallization in the presence of an amine, wherein said crystallization is accompanied by at least one process step corresponding to a washing or sweating operation and removing the amine and recovering purified trioxane.

11. A process for the preparation of highly pure trioxane by crystallization of a trioxane mixture, which comprises adding an amine to the trioxane mixture in the crystallization step or to the apparatus section in which the purity of the trioxane is 95 to 99.0% by weight, said crystallization is accompanied by at least one process step corresponding to a washing or sweating operation.

12. The process as claimed in claim 8, wherein the amine content is from 100 to 5 ppm.

13. The process as claimed in claim 6, in which the purity of the trioxane is from 98 to 99.9% by weight.

* * * * *